United States Patent [19]

Kelly

[11] Patent Number: 5,288,428

[45] Date of Patent: Feb. 22, 1994

[54] LIQUID CRYSTAL COMPOUNDS HAVING A TERMINAL ALKOXY PROPENYL GROUP

[75] Inventor: Stephen Kelly, Möhlin, Switzerland

[73] Assignee: Hoffmann-La Roche Inc., Nutley, N.J.

[21] Appl. No.: 741,029

[22] Filed: Aug. 6, 1991

[30] Foreign Application Priority Data

Aug. 15, 1990 [CH] Switzerland ............. 2651/90

[51] Int. Cl.$^5$ .............. C09K 19/30; C09K 19/34; C09K 19/12; C07C 41/00
[52] U.S. Cl. ............. 252/299.63; 252/299.61; 252/299.66; 568/631; 568/647; 568/667; 568/669; 558/416; 558/425; 570/129; 544/298; 544/224; 359/103
[58] Field of Search .......... 252/299.63, 299.66, 252/299.61, 299.67; 568/647, 667, 669; 359/103; 558/416, 425; 546/339; 570/129; 544/298

[56] References Cited

U.S. PATENT DOCUMENTS

| | | | |
|---|---|---|---|
| 4,130,502 | 12/1978 | Eidenschink et al. | 252/299.63 X |
| 4,468,340 | 8/1984 | Inoue et al. | 252/299.63 |
| 4,564,694 | 1/1986 | Hirai et al. | |
| 4,694,098 | 9/1987 | Hirai et al. | 560/59 |
| 4,709,030 | 11/1987 | Petrzilka et al. | 544/242 |
| 4,886,621 | 12/1989 | Sage et al. | 252/299.61 |
| 4,925,590 | 5/1990 | Reiffenrath et al. | 252/299.61 |
| 5,013,478 | 5/1991 | Petrilka | 252/299.63 |
| 5,032,313 | 7/1991 | Goto et al. | 252/299.63 |
| 5,102,578 | 4/1992 | Buchecker et al. | 252/299.63 |

FOREIGN PATENT DOCUMENTS

| | | |
|---|---|---|
| 058981 | 2/1980 | European Pat. Off. |
| 2636684 | 8/1976 | Fed. Rep. of Germany |
| 3237020 | 10/1982 | Fed. Rep. of Germany |
| 3714043 | 4/1987 | Fed. Rep. of Germany |
| 3807957 | 3/1988 | Fed. Rep. of Germany |
| 3909802 | 7/1988 | Fed. Rep. of Germany |
| 3904817 | 2/1989 | Fed. Rep. of Germany |
| 4027840 | 9/1989 | Fed. Rep. of Germany |
| 89/02884 | 4/1989 | World Int. Prop. O. |
| 89/08622 | 9/1989 | World Int. Prop. O. |
| 89/08687 | 9/1989 | World Int. Prop. O. |
| 89/08689 | 9/1989 | World Int. Prop. O. |
| 90/01021 | 2/1990 | World Int. Prop. O. |

*Primary Examiner*—Robert L. Stoll
*Assistant Examiner*—C. Harris
*Attorney, Agent, or Firm*—George M. Gould; George W. Johnston

[57] ABSTRACT

Compounds having a terminal alkyloxypropenyl group of the general formula

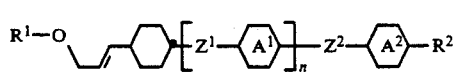

I wherein rings $A^1$ and $A^2$ each independently represent unsubstituted or halogen-substituted 1,4-phenylene, in which optionally 1 CH group or 2 CH groups is/are replaced by nitrogen, or trans-1,4-cyclohexylene or trans-1,3-dioxane-2,5-diyl; n is either 0 or 1; $Z^1$ and $Z^2$ each independently signify a single covalent bond or —$CH_2CH_2$—, —COO—, —OOC—, —$OCH_2$—, —$CH_2O$—, —$(CH_2)_4$—, —$O(CH_2)_3$—, —$(CH_2)_3O$—, the trans form of —O—$CH_2$—CH=CH—, —CH=CH—$CH_2$—O—, —$(CH_2)_2$CH=CH— or —CH=CH—$(CH_2)_2$—; $R^1$ denotes an alkyl group; $R^2$ represents halogen, cyano, trifluoroacetyl, optionally fluorine-substituted alkyl with 1 to 12 carbon atoms, in which optionally 1 —$CH_2$— group or 2 non-adjacent —$CH_2$— groups is/are replaced by oxygen and/or a —$CH_2CH_2$— group is replaced by —CH=CH—, their manufacture, liquid crystalline mixtures which contain these compounds as well as their use for electro-optical purposes.

21 Claims, No Drawings

LIQUID CRYSTAL COMPOUNDS HAVING A TERMINAL ALKOXY PROPENYL GROUP

BACKGROUND

1. Field of the Invention

The present invention pertains to novel compounds having a terminal alkoxypropenyl group, their manufacture, liquid crystalline mixtures which contain these compounds and their use for electro-optical purposes.

2. Description

Liquid crystals are used primarily as dielectrics in indicating devices, since the optical properties of such substances can be influenced by an applied voltage. Such indicating devices are well-known to a person skilled in the art and are, for example, cells having dynamic scattering, DAP cells (deformation of aligned phases), guest/host cells, TN cells having a twisted nematic structure, STN cells ("super twisted nematic"), SBE cells ("super birefringence effect") and OMI cells ("optical mode interference"). The most common indicating devices are based on the Schadt-Helfrich effect and have a twisted nematic structure.

Liquid crystal materials should have a good chemical and thermal stability and, moreover, should be stable to electric fields and electromagnetic radiation. At the usual operating temperatures they should have a suitable mesophase, for example a nematic, cholesteric or tilted smectic phase. Further, the liquid crystal materials should have a low viscosity and in the cells should give short response times, low threshold potentials and a high contrast.

Further properties such as the electrical conductivity, the dielectric anisotropy and the optical anisotropy must fulfil different requirements depending on the type of cell and field of application. For example, for cells having a twisted nematic structure, liquid crystal materials should have a positive dielectric anisotropy and an electrical conductivity which is as low as possible. In addition to the general interest in liquid crystal materials as possible. In addition to the general interest in liquid crystal materials having a high optical anisotropy, there has recently been an increased interest in materials having low optical anisotropy, especially for actively-addressed liquid crystal indicators, e.g. in the case of TFT applications ("thin film transistor") in television sets.

In order to optimize the properties of liquid crystals in the cell, liquid crystals are generally used as mixtures of several components. It is therefore important that the components have a good miscibility with one another. Cholesteric mixtures can preferably consist of one or more optically active dopants and a nematic liquid crystal material.

SUMMARY OF THE INVENTION

The present invention provides compounds of the formula

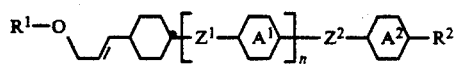

wherein rings $A^1$ and $A^2$ each independently represented unsubstituted or halogen-substituted 1,4-phenylene, in which optionally 1 CH group or 2 CH groups is/are replaced by nitrogen, or trans-1,4-cyclohexylene; or trans-1,3-dioxane-2,5-diyl; n is either 0 or 1; $Z^1$ and $Z^2$ each independently signify a single covalent bond or —CH$_2$CH$_2$—, —COO—, —OOC—, —OCH$_2$—, —CH$_2$O—, —(CH$_2$)$_4$—, —O(CH$_2$)$_3$—, —(CH$_2$)$_3$O—, the trans form of —O—CH$_2$—CH=CH—, —CH=CH—CH$_2$—O—, —(CH$_2$)$_2$CH=CH— or —CH=CH—(CH$_2$)$_2$—; $R^1$ denotes an alkyl group; $R^2$ represents halogen, cyano, trifluoroacetyl, optionally fluorine-substituted alkyl with 1 to 12 carbon atoms, in which optionally 1 —CH$_2$— group or 2 non-adjacent —CH$_2$— groups is/are replaced by oxygen and/or a —CH$_2$CH$_2$— group is replaced by —CH=CH—.

It has been found that the introduction of an alkoxyalkenyl group favorably influences the tendency to form liquid crystal phases and favorably influences the response times. The dielectric anisotropy ($\Delta\epsilon$) and the optical anisotropy ($\Delta n$) can be varied depending on the choice of rings and substituents; thus, for example, compound of formula I in which $R^2$ signifies cyano and $Z^2$ signifies —COO— have a high positive dielectric anisotropy; compounds of formula I in which rings $A^1$ and $A^2$ signify 1,4-phenylene, in which optionally one CH group or two CH groups is/are replaced by nitrogen, have a high positive optical anisotropy.

DETAILED DESCRIPTION OF THE INVENTION

The present invention pertains to compounds of the formula:

wherein rings $A^1$ and $A^2$ each independently are unsubstituted or halogen-substituted 1,4-phenylene, pyridin-2,5-diyl, pyrimidin-2,5-diyl, pyrazin-2,5-diyl or trans-1,4-cyclohexylene or trans-1,3-dioxane-2,5-diyl; n is 0 or 1; $Z^1$ and $Z^2$ each independently are a single covalent bond or —CH$_2$CH$_2$—, —COO—, —OOC—, —OCH$_2$—, —CH$_2$O—, —(CH$_2$)$_4$—, —O(CH$_2$)$_3$—, —(CH$_2$)$_3$O—, the trans form of —O—CH$_2$—CH=CH—, —CH=CH—CH$_2$—O—, —(CH$_2$)$_2$CH=CH— or —CH=CH—(CH$_2$)$_2$—; $R^1$ is alkyl of 1 to 12 carbon atoms; $R^2$ is halogen, cyano, or trifluoroacetyl, or $R^2$ is alkyl, alkoxy, alkenyl, alkenyloxy, alkoxyalkyl, alkoxyalkoxy, alkenyloxy-alkyl, alkenyloxyalkoxy, alkoxyalkenyl or alkoxyalkenyloxy each of such $R^2$ moieties being unsubstituted or fluorine substituted.

As used herein, the term "alkyl" embraces a straight-chain or branched alkyl group with 1-12 carbon atoms.

By the term "alkoxy" what is meant is the group —OX, wherein X is alkyl as defined hereinabove.

As used herein, the term "alkenyl" means a straight-chain or branched alkyl group having at least one double bond. For example, vinyl, 1E-propenyl, 1E-butenyl, 3E-butenyl, 1E-pentenyl, 3E-pentenyl, 1E-hexenyl, 3E-hexenyl, 4-pentenyl, etc.

By the term "alkenyloxy", what is meant is the group —O—Y wherein Y is an alkenyl as defined hereinabove.

As used herein, the term "alkoxyalkyl" means the group —X—O—X wherein X is an alkyl as defined hereinabove.

By the term "alkenyloxyalkyl" what is meant is the group —X—O—Y wherein X is an alkyl and Y is an alkenyl as defined above.

By the term "alkoxyalkoxy" what is meant is the group —O—X—O—X, wherein X is alkyl as defined hereinabove.

As used herein, "alkenyloxyalkoxy" means the group —O—X—O—Y, wherein X and Y are as defined hereinabove.

As used herein "alkoxyalkenyl" means the group —Y—O—X, wherein X and Y are as defined hereinabove.

As used herein "alkoxyalkenyloxy" means the group —O—Y—O—X, wherein X and Y are as defined hereinbefore.

As used herein, "unsubstituted or halogen-substituted 1,4-phenylene, pyridin-2,5-diyl, pyrimidin-2,5-diyl, pyrazin-2,5-diyl" embraces groups such as 1,4-phenylene, 2-fluoro-1,4-phenylene, 2,3-difluoro-1,4-phenylene, 2-chloro-1,4-phenylene, 2-bromo-1,4-phenylene, pyridine-2,5-diyl, pyrimidine-2,5-diyl, pyrazin-2,5-diyl and the like. 1,4-Phenylene, 2-fluoro-1,4-phenylene, 2,3-difluoro-1,4-phenylene, pyridine-2,5-diyl and pyrimidine-2,5-diyl are preferred groups.

The term "halogen" denotes chlorine, fluorine, bromine and iodine, especially chlorine and fluorine.

Moieties designated as $R^2$ include straight-chain and branched (optionally chiral) groups such as alkyl, 1E-alkenyl, 3E-alkenyl, 4-alkenyl, alkenyl having a terminal double bond, alkoxy, alkenyloxy having a terminal double bond, alkoxyalkyl, 2E-alkenyloxy, 3-alkenyloxy, alkenyloxyalkyl, haloalkyl, haloalkoxy and the like. For example, methyl, ethyl, propyl, butyl, pentyl, hexyl, heptyl, octyl, nonyl, decyl, undecyl, dodecyl, vinyl, 1E-propenyl, 1E-butenyl, 1E-pentenyl, 1E-hexenyl, 1E-heptenyl, 3E-pentenyl, 3E-hexenyl, 3E-heptenyl, 4pentenyl, 4Z-hexenyl, 4Z-heptenyl, 5-hexenyl, 6-heptenyl, 7-octenyl, 8-nonenyl, 9-decenyl, 10-undecenyl, 11-dodecenyl, methoxy, ethoxy, propyloxy, butyloxy, pentyloxy, hexyloxy, heptyloxy, octyloxy, nonyloxy, decyloxy, undecyloxy, dodecyloxy, allyloxy, 2E-butenyloxy, 2E-pentenyloxy, 2E-hexenyloxy, 2E-heptenyloxy, 3-butenyloxy, 3Z-pentenyloxy, 3Z-hexenyloxy, 3Z-heptenyloxy, 4-pentenyloxy, 5-hexenyloxy, 6-heptenyloxy, 7-octenyloxy, 8-nonenyloxy, 9-decenyloxy, 10-undecenyloxy, 11-dodecenyloxy, methoxymethyl, ethoxymethyl, propyloxymethyl, fluoromethyl, difluoromethyl, trifluoromethyl, fluoromethoxy, difluoromethoxy and trifluoromethoxy are preferred groups.

A preferred aspect of the invention is concerned with compounds of formula I in which $R^1$ is a straight-chain alkyl group with 1 to 7, preferably 1 to 3, carbon atoms or a branched, optionally chiral, alkyl group with 3 to 7 carbon atoms. The compounds of formula I in which $R^1$ is methyl, ethyl or propyl are particularly preferred.

A preferred aspect of the invention is concerned with compounds of formula I in which one of the groups $Z^1$ and $Z^2$ is a single covalent bond.

A preferred group of compounds of formula I are compounds of the formula

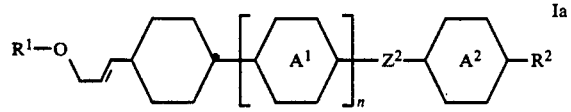

wherein ring $A^1$ is 1,4-phenylene or trans-1,4-cyclohexylene; n is either 0 or 1; ring $A^2$ is unsubstituted or halogen-substituted 1,4-phenylene; and $R^1$, $R^2$ and $Z^2$ are as described above.

A preferred aspect of the invention is concerned with a compound of formula Ia in which $Z^2$ is a single covalent bond, —CH$_2$CH$_2$—, —OOC—, —COO—, —OCH$_2$— or —CH$_2$O—.

Especially preferred compounds of formula Ia are compounds of the formula

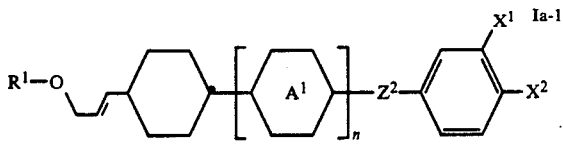

wherein $R^1$ is as defined for formula I; n, $Z^2$ and ring $A^1$ are as defined for formula Ia; $X^1$ is hydrogen, chlorine or fluorine; and $X^2$ is fluorine or chlorine.

$Z^2$ in formula Ia-1 preferably represents a single covalent bond or —CH$_2$CH$_2$—. Because of their low threshold potential the compounds of formula Ia-1 are suitable, for example, for use in liquid crystal materials which are used in TFT cells.

Especially preferred compounds of formula Ia are, compounds of the formula

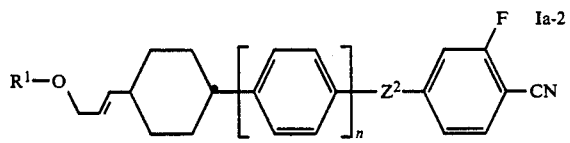

wherein $R^1$ is as defined for formula I; n is either 0 or 1; $Z^2$ is a single covalent bond or —CH$_2$CH$_2$—, —COO—, —OOC—, —OCH$_2$—, —CH$_2$O—, —(CH$_2$)$_4$—, —O(CH$_2$)$_3$—, —(CH$_2$)$_3$O—, the trans form of —O—CH$_2$—CH=CH—, —CH=CH—CH$_2$—O—, —(CH$_2$)$_2$CH=CH— or —CH=CH—(CH$_2$)$_2$—.

$Z^2$ in formula Ia-2 preferably is a single covalent bond, —CH$_2$CH$_2$— or —COO—. The compounds of formula Ia-2 are distinguished, for example, by a comparatively high dielectric anisotropy and a low threshold potential.

Further preferred compounds of formula Ia are compounds of the formula

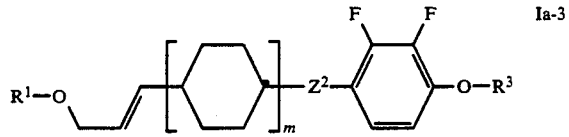

wherein $R^1$ is as defined for formula I; m is either 1 or 2; $Z^2$ is a single covalent bond or —CH$_2$CH$_2$—, —COO—, —OOC—, —OCH$_2$—, —CH$_2$O—, —(CH$_2$)$_4$—, —O(CH$_2$)$_3$—, —(CH$_2$)$_3$O—, the trans form of —O—CH$_2$—CH=CH—, —CH=CH—CH$_2$—O—, —(CH$_2$)$_2$CH=CH— or —CH=CH—(CH$_2$)$_2$—; and $R^3$ is an alkyl of 1-12 carbon atoms, in which optionally —CH$_2$CH$_2$— is replaced by —CH=CH—, or a halo-alkyl group, preferably fluoromethyl, difluoromethyl or trifluoromethyl.

$Z^2$ in formula Ia-3 preferably is a single covalent bond, —$CH_2CH_2$— or —$CH_2O$—. Because of their negative dielectric anisotropy the compounds of formula Ia-3 can be used, for example, for applications in DAP cells (deformation of aligned phases) or ECB cells (electrically controlled birefringence).

A further group of preferred compounds of formula I are compounds of the formula

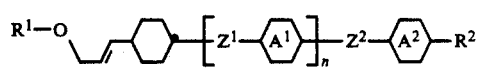

wherein $R^1$ is as defined for formula I; $Z^1$ has the definition given in formula I, preferably a single covalent bond, —$CH_2CH_2$— or —COO—; n is either 0 or 1; and $R^2$ and rings $A^1$ and $A^2$ have the definitions given in formula I.

Especially preferred aspects of the present invention are compounds of formula Ib in which ring $A^1$ is 1,4-phenylene and ring $A^2$ is unsubstituted or halogen-substituted 1,4-phenylene.

The compounds of formula Ib are suitable, for example, for ferroelectric applications, especially preferred compounds of formula Ib being

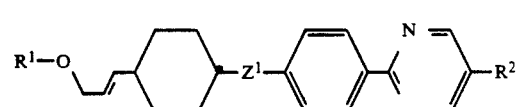

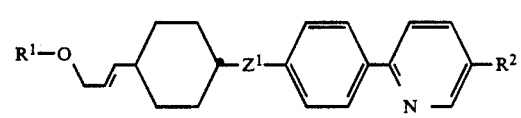

wherein $R^1$ and $R^2$ have the definitions given in formula I; and $Z^1$ has the definition given in formula I and preferably is a single covalent bond or —COO—.

An especially preferred aspect of the invention embraces compounds of formulae I, Ia, Ia-1 to 3 and Ib, Ib-1 and Ib-2 in which $R^1$ is either methyl, ethyl or propyl.

The present invention therefore provides novel components for further optimizing and modifying liquid crystal materials.

The compounds of formula I can be manufactured in accordance with the invention in a manner known per se, for example according to the methods illustrated in Scheme 1 and according to the methods illustrated in the Examples.

Scheme 1

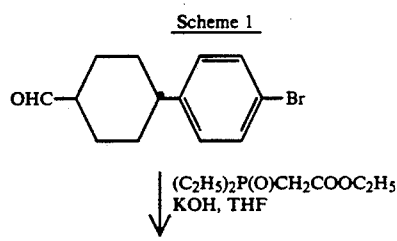

Scheme 1

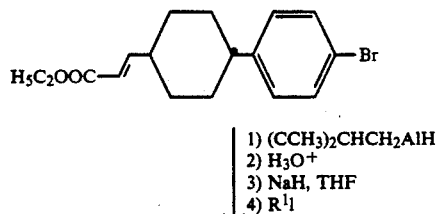

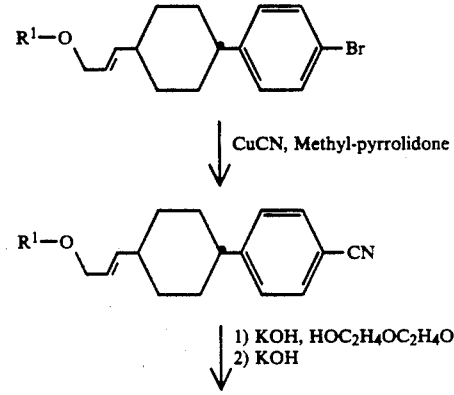

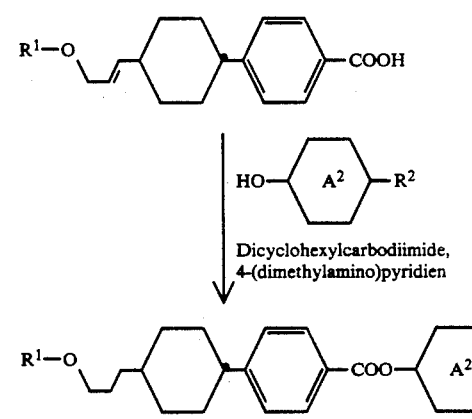

The compound of formula I can be used in the form of mixtures with one another and/or with other liquid crystal components.

The liquid crystalline mixtures in accordance with the invention contain at least two components, of which at least one component is a compound of formula I. A second component and optionally additional components can be further compounds of formula I or other liquid crystal components.

Having regard to the good solubility of the compounds of formula I and having regard to their good miscibility with one another, they can be present in the mixtures in accordance with the invention in relatively high amounts. In general, however, an amount of about 1–50 wt. %, especially about 5–30 wt. %, of compounds of formula I is preferred.

The mixtures in accordance with the invention preferably contain, in addition to one or more compounds of formula I, one or more compounds from the group of compounds of the formulae

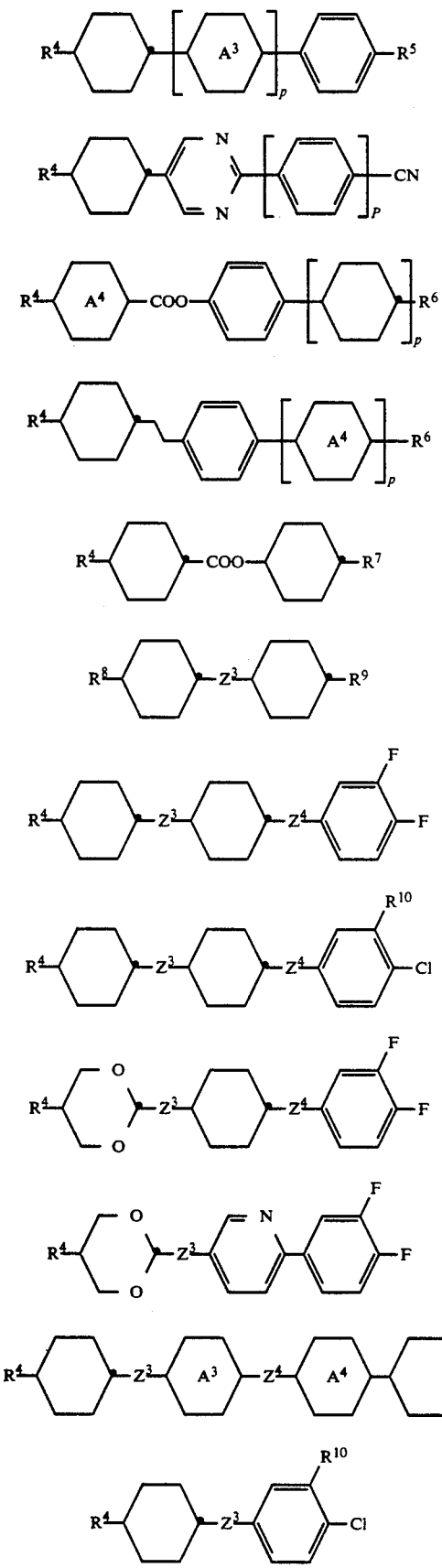
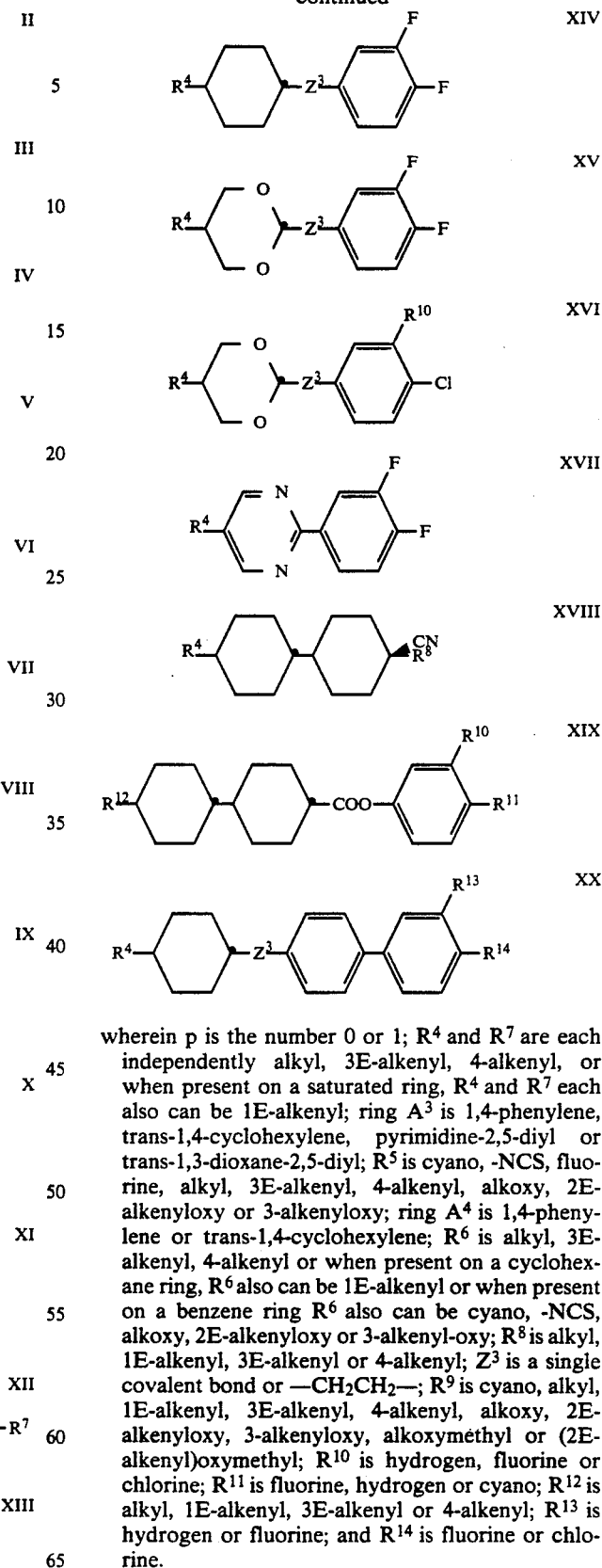

wherein p is the number 0 or 1; $R^4$ and $R^7$ are each independently alkyl, 3E-alkenyl, 4-alkenyl, or when present on a saturated ring, $R^4$ and $R^7$ each also can be 1E-alkenyl; ring $A^3$ is 1,4-phenylene, trans-1,4-cyclohexylene, pyrimidine-2,5-diyl or trans-1,3-dioxane-2,5-diyl; $R^5$ is cyano, -NCS, fluorine, alkyl, 3E-alkenyl, 4-alkenyl, alkoxy, 2E-alkenyloxy or 3-alkenyloxy; ring $A^4$ is 1,4-phenylene or trans-1,4-cyclohexylene; $R^6$ is alkyl, 3E-alkenyl, 4-alkenyl or when present on a cyclohexane ring, $R^6$ also can be 1E-alkenyl or when present on a benzene ring $R^6$ also can be cyano, -NCS, alkoxy, 2E-alkenyloxy or 3-alkenyl-oxy; $R^8$ is alkyl, 1E-alkenyl, 3E-alkenyl or 4-alkenyl; $Z^3$ is a single covalent bond or —CH$_2$CH$_2$—; $R^9$ is cyano, alkyl, 1E-alkenyl, 3E-alkenyl, 4-alkenyl, alkoxy, 2E-alkenyloxy, 3-alkenyloxy, alkoxymethyl or (2E-alkenyl)oxymethyl; $R^{10}$ is hydrogen, fluorine or chlorine; $R^{11}$ is fluorine, hydrogen or cyano; $R^{12}$ is alkyl, 1E-alkenyl, 3E-alkenyl or 4-alkenyl; $R^{13}$ is hydrogen or fluorine; and $R^{14}$ is fluorine or chlorine.

The above term "saturated ring" denotes trans-1,4-cyclohexylene and trans-1,3-dioxane-2,5-diyl. Groups $R^4$ to $R^9$ each preferably have a maximum of 12 carbon atoms, especially a maximum of 7 carbon atoms. Straight-chain groups are generally preferred. The compounds of formulae II-XX are known and in part are commercially available.

The manufacture of the liquid crystalline mixtures and of the electrooptical devices can be effected in a manner known per se.

The invention is illustrated in more detail by the following Examples. In the Examples, C denotes a crystalline phase, N denotes a nematic phase, S signifies a smectic phase and I denotes the isotropic phase. $V_{10}$ denotes the voltage for 10% transmission, $t_{on}$ and $t_{off}$ denote, respectively, the switching-on time and the switching-off time. $\Delta$n denotes the optical anisotropy. Unless otherwise stated, the following examples were carried out as stated.

EXAMPLE 1

A mixture of 0.5 g of sodium hydride and 50 ml of tetrahydrofuran was treated with 2.6 g of 1-bromo-4-[trans-4-[(E)-3-hydroxypropenyl]cyclohexyl]benzene while gassing with nitrogen, stirred for 2 hours, treated with 1.6 g of methyl iodide and subsequently stirred at room temperature overnight. The reaction mixture was treated with 500 ml of water and extracted four times with 50 ml of hexane each time, the combined organic phases were washed twice with 500 ml of water each time, dried over magnesium sulphate, the suspension was filtered and the filtrate was concentrated. The residue was purified by chromatography on silica gel with hexane and the product obtained was recrystallized from hexane at $-78°$ C. to give 2.4 g of 1-bromo-4-[trans-4-[(E)-3-methoxypropenyl]cyclohexyl]benzene, m.p. (C-I) 47° C.

The 1-bromo-4-[trans-4-[(E)-3-hydroxypropenyl]cyclo-hexyl]benzene used as the starting material was prepared as follows:

a) 20.4 g of triphenyl-methoxymethyl-phosphonium chloride were suspended in 60 ml of t-butyl methyl ether while gassing with argon in a sulphonation flask having a thermometer, mechanical stirrer, dropping funnel and solid substance addition tube and treated at $-10°$ C. within 10 minutes with 6.6 g of solid potassium t-butylate. After completion of the addition the mixture was stirred at $-10°$ C. to 0° C. for 30 minutes, then the deep orange, heterogeneous reaction mixture was treated dropwise at 0° C. with a solution of 10 g of 4-(4-bromophenyl)cyclohexanone in 50 ml of absolute tetrahydrofuran, subsequently stirred at room temperature for 24 hours, poured into 500 ml of hexane and filtered. Low-pressure chromatography of the concentrated residue (13.9 g) on silica gel with hexane/ethyl acetate (vol. 9:1) gave 10.4 g of 1-bromo-4-[4-(methoxymethylidene)cyclohexyl]benzene as a colourless oil.

b) A mixture of 10.4 g of 1-bromo-4-[4-(methoxymethyli-dene)cyclohexyl]benzene and 100 ml of tetrahydrofuran/2N hydrochloric acid (vol. 4:1) was heated to reflux for 30 minutes in a round flask. Subsequently, the reaction mixture was poured into 100 ml of water and extracted three times with 100 ml of diethyl ether each time. The organic phases were washed with 100 ml of water, dried over magnesium sulphate and concentrated. There were obtained 9.4 g of 4-(4-bromophenyl)cyclohexanecarboxaldehyde as white crystals; trans/cis ratio about 5:3.

c) A mixture of 9.1 g of 4-(4-bromophenyl)cyclohexanecarb-oxaldehyde and 3.8 g of powdered potassium hydroxide in 200 ml of tetrahydrofuran was placed at room temperature in a sulphonation flask while gassing with argon and treated with 9.2 g of triethyl phosphonoacetate within 15 minutes, stirred overnight, taken up in 100 ml of water and extracted three times with 100 ml of methylene chloride each time. The organic phases were washed twice with 100 ml of water each time, dried over magnesium sulphate and concentrated. Low-pressure chromato-graphy of the residue (12 g) on silica gel with hexane/ethyl acetate (vol. 9:1) gave 11.7 g of ethyl (E)-3-[trans-4-(4-bromo-phenyl)cyclohexyl]acrylate as colourless crystals.

d) A solution of 12.7 g of ethyl (E)-3-[trans-4-(4-bromo-phenyl)cyclohexyl]acrylate in 225 ml of toluene was placed at 0° C. while gassing with argon in a sulphonation flask having a thermometer and serum cap and treated within 10 minutes with 47.0 ml of a 1.2M solution of diisobutylaluminium hydride in toluene. After completion of the addition the reaction mixture was stirred at room temperature overnight before it was poured into 100 ml of 1.0N sulphuric acid and extracted twice with 50 ml of ethyl acetate each time. The organic phases were washed with 50 ml of water, dried over magnesium sulphate and concen-trated. The residue (10.9 g) was purified by chromatography on silica gel with hexane/ethyl acetate (vol. 7:3). The resulting 1-bromo-4-[trans-4-[(E)-3-hydroxypropenyl]cyclohexyl]-benzene was recrystallized twice from cyclohexane. This gave 2.6 g of pure product with m.p. 104° C.

The following compounds can be manufactured in an analogous manner:

1-Fluoro-4-[trans-4-[(E)-3-methoxypropenyl]cyclohex-yl]-benzene, m.p. (C-I) 27° C.;

1-chloro-4-[trans-4-[(E)-3-methoxypropenyl]cyclohex-yl]-benzene, m.p. (C-I) 40° C.;

1-bromo-4-[trans-4-[(E)-3-methoxypropenyl]cyclohex-yl]-benzene, m.p. (C-I) 47° C.;

1-chloro-2-fluoro-4-[trans-4-[(E)-3-methoxypropenyl]-cyclohexyl]benzene, m.p. (C-I) 23° C.;

1,2-difluoro-4-[trans-4-[(E)-3-methoxypropenyl]cyclo-hexyl]benzene, m.p. (C-I) 24° C.;

1-methyl-4-[trans-4-[(E)-3-methoxypropenyl]cyclohex-yl]-benzene;

1-ethyl-4-[trans-4-[(E)-3-methoxypropenyl]cyclohex-yl]-benzene;

1-propyl-4-[trans-4-[(E)-3-methoxypropenyl]cyclohex-yl]-benzene;

1-methoxy-4-[trans-4-[(E)-3-methoxypropenyl]cy-clohexyl]-benzene, m.p. (C-I) 24° C., cl.p. (N-I) (17° C.);

1-ethoxy-4-[trans-4-[(E)-3-methoxypropenyl]cyclohex-yl]-benzene, m.p. (C-N) 19° C., cl.p. (N-I) 46° C.;

1-propyloxy-4-[trans-4-[(E)-3-methoxypropenyl]cy-clohexyl]-benzene, m.p. (C-I) 30° C., cl.p. (N-I) (19° C.);

1-butyloxy-4-[trans-4-[(E)-3-methoxypropenyl]cy-clohexyl]-benzene, m.p. (C-N) 23° C., cl.p. (N-I) 40° C.;

1-pentyloxy-4-[trans-4-[(E)-3-methoxypropenyl]cy-clohexyl]-benzene, m.p. (C-N) 30° C., cl.p. (N-I) 31° C.;

1-hexyloxy-4-[trans-4-[(E)-3-methoxypropenyl]cy-clohexyl]-benzene, m.p. (C-$S_B$) 16° C., ($S_B$-N) 30° C., cl.p. (N-I) 38° C.;

1-heptyloxy-4-[trans-4-[(E)-3-methoxypropenyl]cy-clohexyl]-benzene, m.p. (C-$S_B$) 14° C., cl.p. ($S_B$-I) 38° C.;

1-(trifluoromethyl)-4-[trans-4-[(E)-3-methoxypropenyl]cyclohexyl]benzene;

1-(trifluoromethoxy)-4-[trans-4-[(E)-3-methoxypropenyl]-cyclohexyl]benzene;

1-(difluoromethoxy)-4-[trans-4-[(E)-3-methoxypropenyl]-cyclohexyl]benzene;

1-fluoro-4-[trans-4-(trans-4-[(E)-3-methoxypropenyl]-cyclohexyl)cyclohexyl]benzene, m.p. (C-N) 83° C., cl.p. (N-I) 170° C.;

1-chloro-4-[trans-4-(trans-4-[(E)-3-methoxypropenyl]-cyclohexyl)cyclohexyl]benzene;

1-bromo-4-[trans-4-(trans-4-[(E)-3-methoxypropenyl]-cyclohexyl)cyclohexyl]benzene, m.p. (C-N) 120° C., cl.p. (N-I) 207° C.;

1-chloro-2-fluoro-4-[trans-4-(trans-4-[(E)-3-methoxypropenyl]cyclohexyl)cyclohexyl]benzene, m.p. (C-N) 60° C., cl.p. (N-I) 168° C.;

1-(trifluoroacetyl)-4-[trans-4-(trans-4-[(E)-3-methoxypropenyl]cyclohexyl)cyclohexyl]benzene:

1,2-difluoro-4-[trans-4-(trans-4-[(E)-3-methoxypropenyl]cyclohexyl)cyclohexyl]benzene, m.p. (C-N) 47° C., cl.p. (N-I) 133° C.;

1-methyl-4-[trans-4-(trans-4-[(E)-3-methoxypropenyl]-cyclohexyl)cyclohexyl]benzene, m.p. (C-$S_B$) 79° C., ($S_B$-N) 99° C., cl.p. (N-I) 193° C.

1-ethyl-4-[trans-4-(trans-4-[(E)-3-methoxypropenyl]-cyclohexyl)cyclohexyl]benzene;

1-propyl-4-[trans-4-(trans-4-[(E)-3-methoxypropenyl]-cyclohexyl)cyclohexyl]benzene;

1-methyl-2-fluoro-4-[trans-4-(trans-4-[(E)-3-methoxypropenyl]cyclohexyl)cyclohexyl]benzene, m.p. (C-N) 58° C., cl.p. (N-I) 160° C.;

1-(trifluoromethyl)-4-[trans-4-(trans-4-[(E)-3-methoxypropenyl]cyclohexyl)cyclohexyl]benzene;

1-(trifluoromethoxy)-4-[trans-4-(trans-4-[(E)-3-methoxypropenyl]cyclohexyl)cyclohexyl]benzene;

1-(difluoromethoxy)-4-[trans-4-(trans-4-[(E)-3-methoxypropenyl]cyclohexyl)cyclohexyl]benzene;

1-(trifluoroacetyl)-4-[trans-4-(trans-4-[(E)-3-methoxypropenyl]cyclohexyl)cyclohexyl]benzene;

1-fluoro-4-[2-(trans-4-[(E)-3-methoxypropenyl]cyclohexyl)ethyl]benzene;

1-chloro-4-[2-(trans-4-[(E)-3-methoxypropenyl]cyclohexyl)ethyl]benzene;

1-chloro-2-fluoro-4-[2-(trans-4-[(E)-3-methoxypropenyl]-cyclohexyl)ethyl]benzene;

1,2-difluoro-4-[2-(trans-4-[(E)-3-methoxypropenyl]cyclohexyl)ethyl]benzene;

1-(trifluoromethyl)-4-[2-(trans-4-[(E)-3-methoxypropenyl]cyclohexyl)ethyl]benzene;

1-(trifluoromethoxy)-4-[2-(trans-4-[(E)-3-methoxypropenyl]cyclohexyl)ethyl]benzene;

1-(difluoromethoxy)-4-[2-(trans-4-[(E)-3-methoxypropenyl]cyclohexyl)ethyl]benzene;

1-(trifluoroacetyl)-4-[2-(trans-4-[(E)-3-methoxypropenyl]cyclohexyl)ethyl]benzene;

1-fluoro-4-(2-[trans-4-(trans-4-[(E)-3-methoxypropenyl]cyclohexyl)cyclohexyl]ethyl)benzene;

1-chloro-4-(2-[trans-4-(trans-4-[(E)-3-methoxypropenyl]cyclohexyl)cyclohexyl]ethyl)benzene;

1-chloro-2-fluoro-4-(2-[trans-4-(trans-4-[(E)-3-methoxypropenyl]cyclohexyl)cyclohexyl]ethyl)benzene;

1,2-difluoro-4-(2-[trans-4-(trans-4-[(E)-3-methoxypropenyl]cyclohexyl)cyclohexyl]ethyl)benzene;

1-(trifluoromethyl)-4-(2-[trans-4-(trans-4-[(E)-3-methoxypropenyl]cyclohexyl)cyclohexyl]ethyl)benzene;

1-(trifluoromethoxy)-4-(2-[trans-4-(trans-4-[(E)-3-methoxypropenyl]cyclohexyl)cyclohexyl]ethyl)benzene;

1-(difluoromethoxy)-4-(2-[trans-4-(trans-4-[(E)-3-methoxypropenyl]cyclohexyl)cyclohexyl]ethyl)benzene;

1-(trifluoroacetyl)-(2-[trans-4-(trans-4-[(E)-3-methoxypropenyl]cyclohexyl)cyclohexyl]ethyl)benzene;

1-methoxy-2,3-difluoro-4-[(trans-4-[(E)-3-methoxypropenyl]cyclohexyl)methoxy]benzene;

1-ethoxy-2,3-difluoro-4-[(trans-4-[(E)-3-methoxypropenyl]cyclohexyl)methoxy]benzene;

1-propyloxy-2,3-difluoro-4-[(trans-4-[(E)-3-methoxypropenyl]cyclohexyl)methoxy]benzene;

1-butyloxy-2,3-difluoro-4-[(trans-4-[(E)-3-methoxypropenyl]cyclohexyl)methoxy]benzene;

1-methoxy-2,3-difluoro-4-{[trans-4-(trans-4-[(E)-3-methoxypropenyl]cyclohexy)cyclohexyl]methoxy} benzene;

trans-1-[trans-4-[(E)-3-methoxypropenyl]cyclohexyl]-4-propylcyclohexane, m.p. (C-$S_B$) 32° C., ($S_B$-N) 70° C., cl.p. (N-I) 73° C.;

trans-1-[trans-4-[(E)-3-ethoxypropenyl]cyclohexyl]-4-propylcyclohexane;

trans-1-[trans-4-[(E)-3-propyloxypropenyl]cyclohexyl]-4-propylcyclohexane;

trans-1-[trans-4-[(E)-3-methoxypropenyl]cyclohexyl]-4-pentylcyclohexane;

trans-1-[trans-4-[(E)-3-ethoxypropenyl]cyclohexyl]-4-pentylcyclohexane;

trans-1-[trans-4-[(E)-3-propyloxypropenyl]cyclohexyl]-4-pentylcyclohexane;

trans-1-[trans-4-[(E)-3-methoxypropenyl]cyclohexyl]-4-vinylcyclohexane, m.p. (C-$S_B$) 9° C., ($S_B$-N) 18° C., cl.p. (N-I) 36° C.;

trans-1-[trans-4-[(E)-3-methoxypropenyl]cyclohexyl]-4-[(E)-propenyl]cyclohexane, m.p. (C-N) 10° C., cl.p. (N-I) 89° C.;

trans-1-[trans-4-[(E)-3-methoxypropenyl]cyclohexyl]-4-[3-butenyl]cyclohexane, m.p. (C-$S_B$) −17° C., ($S_B$-N) 67° C., cl.p. (N-I) 75° C.;

trans-1-[trans-4-[(E)-3-methoxypropenyl]cyclohexyl]-4-[3E-pentenyl]cyclohexane, m.p. (C-$S_B$) 39° C., ($S_B$-N) 71° C., cl.p. (N-I) 100° C.;

trans-1-[trans-4-[(E)-3-methoxypropenyl]cyclohexyl]-4-[4-pentenyl]cyclohexane, m.p. (C-$S_B$) 13° C., cl.p. $S_B$-I) 89° C.;

trans-1-[trans-4-[(E)-3-ethoxypropenyl]cyclohexyl]-4-[(E)-propenyl]cyclohexane;

trans-1-[trans-4-[(E)-3-propyloxypropenyl]cyclohexyl]-4-[(E)-propenyl]cyclohexane;

4′-chloro-4-[trans-4-[(E)-3-methoxypropenyl]cyclohexyl]-biphenyl, m.p. (C-N) 140° C., cl.p. (N-I) 208° C.;

4′-fluoro-4-[trans-4-[(E)-3-methoxypropenyl]cyclohexyl]-biphenyl, m.p. (C-N) 111° C., cl.p. (N-I) 174° C.;

4′-(trifluoromethyl)-4-[trans-4-[(E)-3-methoxypropenyl]cyclohexyl]biphenyl;

4′-(trifluoromethoxy)-4-[trans-4-[(E)-3-methoxypropenyl]cyclohexyl]biphenyl;

4′-(difluoromethoxy)-4-[trans-4-[(E)-3-methoxypropenyl]cyclohexyl]biphenyl;

4′-(trifluoroacetyl)-4-[trans-4-[(E)-3-methoxypropenyl]-cyclohexyl]biphenyl;

4′-chloro-3′-fluoro-4-[trans-4-[(E)-3-methoxypropenyl]-cyclohexyl]biphenyl, m.p. (C-N) 105° C., cl.p. (N-I) 153° C.;

3′,4′-difluoro-4-[trans-4-[(E)-3-methoxypropenyl]cyclohexyl]biphenyl, m.p. (C-N) 91° C., cl.p. (N-I) 107° C.;

5-propyl-2-[4-(trans-4-[(E)-3-methoxypropenyl]cyclohexyl)phenyl]pyrimidine;

5-butyl-2-[4-(trans-4-[(E)-3-methoxypropenyl]cyclohexyl)phenyl]pyrimidine;
5-pentyl-2-[4-(trans-4-[(E)-3-methoxypropenyl]cyclohexyl)phenyl]pyrimidine;
5-hexyl-2-[4-(trans-4-[(E)-3-methoxypropenyl]cyclohexyl)phenyl]pyrimidine;
5-heptyl-2-[4-(trans-4-[(E)-3-methoxypropenyl]cyclohexyl)phenyl]pyrimidine;
5-propyl-2-[4-(trans-4-[(E)-3-methoxypropenyl]cyclohexyl)phenyl]pyridine;
5-butyl-2-[4-(trans-4-[(E)-3-methoxypropenyl]cyclohexyl)phenyl]pyridine;
5-pentyl-2-[4-(trans-4-[(E)-3-methoxypropenyl]cyclohexyl)phenyl]pyridine;
5-hexyl-2-[4-(trans-4-[(E)-3-methoxypropenyl]cyclohexyl)phenyl]pyridine;
5-heptyl-2-[4-(trans-4-[(E)-3-methoxypropenyl]cyclohexyl)phenyl]pyridine;

EXAMPLE 2

A mixture of 2.3 g of 1-bromo-4-[trans-4-[(E)-3-methoxy propenyl]cyclohexyl]benzene, 1.7 g of copper(I) cyanide and 45 ml of 1-methyl-2-pyrrolidone was heated at 180° C. for 2.5 hours while gassing with argon. The cooled reaction mixture was added to a solution of 1.7 g of iron(III) chloride, 1 ml of concentrated hydrochloric acid and 20 ml of water, stirred at 55°-60° C. for 20 minutes, cooled and subsequently extracted three times with 50 ml of ethyl acetate each time. The combined organic phases were washed twice with 100 ml of concentrated sodium chloride solution each time, dried over magnesium sulphate, filtered and concentrated. The residue was purified by chromatography on silica gel with hexane/ethyl acetate (vol. 9:1). The resulting 4-[trans-4-[(E)-3-methoxypropenyl]cyclohexyl]benzonitrile was recrystallized from hexane. This gave 0.8 g of pure product with m.p. (C-I) 66° C. and cl.p. (N-I) 59° C.

The following compounds can be manufactured in an analogous manner:
4-[trans-4-[(E)-3-Ethoxypropenyl]cyclohexyl]benzonitrile;
4-[trans-4-[(E)-3-propyloxypropenyl]cyclohexyl]benzonitrile;
3-fluoro-4-[trans-4-[(E)-3-methoxypropenyl]cyclohexyl]-benzonitrile;
3-fluoro-4-[trans-4-[(E)-3-ethoxypropenyl]cyclohexyl]-benzonitrile;
3-fluoro-4-[trans-4-[(E)-3-propyloxypropenyl]cyclohexyl]-benzonitrile;
4-[trans-4-[(E)-3-methoxypropenyl]cyclohexyl)cyclohexyl]benzonitrile;
4-[trans-4-(trans-4-[(E)-3-ethoxypropenyl]cyclohexyl)cyclohexyl]benzonitrile;
4-[trans-4-(trans-4-[(E)-3-propyloxypropenyl]cyclohexyl)cyclohexyl]benzonitrile;
3-fluoro-4-[trans-4-[(E)-3-methoxypropenyl]cyclohexyl)cyclohexyl]benzonitrile;
3-fluoro-4-[trans-4-(trans-4-[(E)-3-ethoxypropenyl]cyclohexyl)cyclohexyl]benzonitrile;
3-fluoro-4-[trans-4-(trans-4-[(E)-3-propyloxypropenyl]cyclohexyl)cyclohexyl]benzonitrile;
4-[2-(trans-4-[(E)-3-methoxypropenyl]cyclohexyl)ethyl]-benzene;
4-(2-[trans-4-(trans-4-[(E)-3-methoxypropenyl]cyclohexyl)cyclohexyl]ethyl)benzene.

EXAMPLE 3

0.6 g of 4-[trans-4-[(E)-3-methoxypropenyl]cyclohexyl]-benzoic acid, 0.3 g of 4-hydroxybenzonitrile and 0.04 g of 4-(dimethylamino)pyridine were dissolved in 50 ml of dichloro-methane, the solution was treated portionwise with 0.6 g of N,N'-dicyclohexylcarbodiimide within 10 minutes while stirring, the mixture was stirred at room temperature overnight and then filtered. The filtrate was diluted with dichloromethane, washed twice with 50 ml of saturated sodium carbonate solution each time and once with water, dried over magnesium sulphate, filtered and concentrated. The crude product obtained was purified by chromatography on silica gel with hexane/ethyl acetate (vol. 9:1). The 4-[trans-4-[(E)-3-methoxypropenyl]cyclohexyl]benzoic acid 4-cyanophenyl ester was recrystallized from methanol. This gave 0.6 g of pure product with m.p. (C-N) 147° C. and cl.p. (N-I) 253° C.

The 4-[trans-4-[(E)-3-methoxypropenyl]cyclohexyl]-benzoic acid used as the starting material was prepared as follows:

A mixture of 0.6 g of 4-[trans-4-[(E)-3-methoxypropenyl]cyclohexyl]benzonitrile, 20 ml of ethylene glycol and 1.5 g of potassium hydroxide was heated to 180° C. for 3.5 hours. After cooling the mixture was poured into 300 ml of water and acidified with 3N hydrochloric acid. The separated 4-[trans-4-[(E)-3-methoxypropenyl]cyclohexyl]benzoic acid was taken up in diethyl ether, washed neutral with water, dried with sodium sulphate and concentrated. Recrystallization of the residue from ethanol gave 0.4 g of pure product.

The following compounds can be manufactured in an analogous manner:
4-[trans-4-[(E)-3-Methoxypropenyl]cyclohexyl]benzoic acid 4-fluorophenyl ester, m.p. (C-N) 129° C., cl.p. (N-I) 187° C.;
4-[trans-4-[(E)-3-methoxypropenyl]cyclohexyl]benzoic acid 4-chlorophenyl ester;
4-[trans-4-[(E)-3-methoxypropenyl]cyclohexyl]benzoic acid 4-bromophenyl ester;
4-[trans-4-[(E)-3-methoxypropenyl]cyclohexyl]benzoic acid 3,4-difluorophenyl ester, m.p. (C-N) 99° C., cl.p. (N-I) 149° C.;
4-[trans-4-[(E)-3-methoxypropenyl]cyclohexyl]benzoic acid 4-(trifluoromethoxy)phenyl ester, m.p. (C-N) 120° C. (N-I) 187° C.;
4-[trans-4-[(E)-3-methoxypropenyl]cyclohexyl]benzoic acid 2,3-difluoro-4-ethoxyphenyl ester;
4-[trans-4-[(E)-3-methoxypropenyl]cyclohexyl]benzoic acid 3-fluoro-4-cyanophenyl ester;
4-[trans-4-[(E)-3-methoxypropenyl]cyclohexyl]benzoic acid 4-methylphenyl ester;
4-[trans-4-[(E)-3-methoxypropenyl]cyclohexyl]benzoic acid 4-ethylphenyl ester;
4-[trans-4-[(E)-3-methoxypropenyl]cyclohexyl]benzoic acid 4-propylphenyl ester;
4-[trans-4-[(E)-3-methoxypropenyl]cyclohexyl]benzoic acid 4-methoxyphenyl ester;
4-[trans-4-[(E)-3-methoxypropenyl]cyclohexyl]benzoic acid 4-ethoxyphenyl ester;
4-[trans-4-[(E)-3-methoxypropenyl]cyclohexyl]benzoic acid 4-cyanophenyl ester, m.p. (C-N) 147° C., cl.p. (N-I) 253° C.;
4-[trans-4-[(E)-3-methoxypropenyl]cyclohexyl]benzoic acid 4-cyano-3-fluorophenyl ester, m.p. (C-N) 94° C., cl.p. (N-I) 214° C.

EXAMPLE 4

The properties of the compounds were investigated by preparing binary mixtures with 4-(trans-4-pentylcyclohexyl)-benzonitrile and measuring their threshold potential and response times in a TN cell (low bias tilt) having a plate separation of 8 mm; the 2.5-fold value of the threshold potential being chosen as the operating voltage. The corresponding data for pure 4-(trans-4-pentylcyclohexyl)benzonitrile are: cl.p. (N-I) 54.6° C., $V_{10}=1.62$ V, $t_{on}=22$ ms, $t_{off}=40$ ms, Dn=0.120.

Mixture A 90 wt. % of 4-(trans-4-pentylcyclohexyl)benzonitrile.
10 wt. % of 1-fluoro-4-[trans-4-(trans-4-[(E)-3-methoxypropenyl]cyclohexyl]cyclohexyl]benzene.

cl.p. (N-I)=61° C., $V_{10}=1.51$ V, $t_{on}=36$ ms, $t_{off}=58$ ms, $\Delta n=0.121$.

Mixture B 80 wt. % of 4-(trans-4-pentylcyclohexyl)benzonitrile.
20 wt. % of 1-fluoro-4-[trans-4-(trans-4-[(E)-3-methoxy-propenyl]cyclohexyl]cyclohexyl]benzene.

cl.p. (N-I)=67.3° C., $V_{10}=1.56$ V, $t_{on}=53$ ms, $t_{off}=89$ ms, $\Delta n=0.119$.

Mixture C 90 wt. % of 4-(trans-4-pentylcyclohexyl)benzonitrile.
10 wt. % of 1,2-difluoro-4-[trans-4-[(E)-3-methoxypropenyl]cyclohexyl]cyclohexyl]benzene.

cl.p. (N-I)=58.9° C., $V_{10}=1.6$ V, $t_{on}=33$ ms, $t_{off}=46$ ms, $\Delta n=0.121$.

Mixture D 80 wt. % of 4-(trans-4-pentylcyclohexyl)benzonitrile.
20 wt. % of 1,2-difluoro-4-[trans-4-(trans-4-[(E)-3-methoxypropenyl]cyclohexyl]cyclohexyl]benzene.

cl.p. (N-I)=63.8° C., $V_{10}=1.86$ V, $t_{on}=32$ ms, $t_{off}=47$ ms, $\Delta n=0.119$.

What is claimed is:
1. A compound of the formula

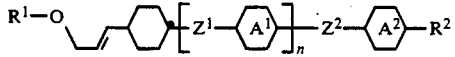

wherein rings $A^1$ and $A^2$ each independently are unsubstituted or halogen-substituted 1,4-phenylene, pyridin-2,5-diyl, pyrimidin-2,5-diyl, pyrazin-2,5-diyl or trans-1,4-cyclohexylene or trans-1,3-dioxane-2,5-diyl; n is 0 or 1; $Z^1$ and $Z^2$ each independently are a single covalent bond or —CH$_2$CH$_2$—, —COO—, —OOC—, —OCH$_2$—, —CH$_2$O—, —(CH$_2$)$_4$—, —O(CH$_2$)$_3$—, —(CH$_2$)$_3$O—, the trans form of —O—CH$_2$—CH=CH—, —CH=CH—CH$_2$—O—, —(CH$_2$)$_2$CH=CH— or —CH=CH—(CH$_2$)$_2$—; $R^1$ is alkyl of 1 to 12 carbon atoms; $R^2$ is halogen, cyano, or trifluoroacetyl, or $R^2$ is alkyl, alkoxy, alkenyl, alkenyloxy, alkoxyalkyl, alkoxyalkoxy, alkenyloxyalkyl, alkenyloxyalkoxy, alkyloxyalkenyl or alkyloxyalkenyloxy, each of such $R^2$ moieties being unsubstituted or fluorine substituted.

2. A compound according to claim 1, wherein $R^1$ is alkyl with 1 to 7 carbon atoms.

3. A compound according to claim 1, wherein one of the groups $Z^1$ and $Z^2$ is a single covalent bond.

4. A compound according to claim 3, wherein $Z^1$ is a single covalent bond; ring $A^1$ is either 1,4-phenylene or trans-1,4-cyclohexylene; n is 0 or 1; and ring $A^2$ is unsubstituted or halogen-substituted 1,4-phenylene.

5. A compound according to claim 4, wherein ring $A^2$ is 1,4-phenylene which is unsubstituted or substituted with chlorine or fluorine, and $R^2$ is fluorine or chlorine.

6. A compound according to claim 1, wherein ring $A^1$ is 1,4-phenylene; $Z^1$ is a single covalent bond; $Z^2$ is either a single covalent bond, —CH$_2$—CH$_2$—, or —COO—; ring $A^2$ is fluoro-1,4-phenylene; and $R^2$ is cyano.

7. A compound according to claim 1, wherein $Z^2$ is either a single covalent bond, —CH$_2$CH$_2$— or —COO—; ring $A^2$ is 2,3-difluoro-1,4-phenylene; and $R^2$ is a haloalkoxy group of 1 to 12 carbon atoms, alkoxy of 1 to 12 atoms or alkenyloxy.

8. A compound according to claim 1, wherein $Z^1$ is either a single covalent bond, —CH$_2$—CH$_2$—, or —COO—.

9. A compound according to claim 1, wherein ring $A^1$ is unsubstituted 1,4-phenylene; $Z^2$ is a single covalent bond; and ring $A^2$ is pyrimidine-2,5-diyl.

10. A compound according to claim 1, wherein ring $A^1$ is unsubstituted 1,4-phenylene; $Z^2$ is a single covalent bond; and ring $A^2$ is pyridin-2,5-diyl.

11. A compound according to claim 9, wherein $Z^1$ is —COO—.

12. A compound according to claim 10, wherein $Z^1$ is —COO—.

13. A liquid crystalline mixture with at least two components, wherein at least one component is a compound of the formula

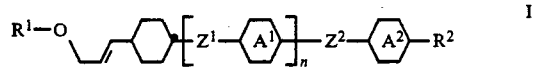

wherein rings $A^1$ and $A^2$ each independently are unsubstituted or halogen-substituted 1,4-phenylene, pyridin-2,5-diyl, pyrimidin-2,5-diyl, pyrazin-2,5-diyl or trans-1,4-cyclohexylene or trans-1,3-dioxane; n is 0 or 1; $Z^1$ and $Z^2$ each independently are a single covalent bond or —CH$_2$CH$_2$—, —COO—, —OOC—, —OCH$_2$—, —CH$_2$O—, —(CH$_2$)$_4$—, —O(CH$_2$)$_3$—, —(CH$_2$)$_3$O—, the trans form of —O—CH$_2$—CH=CH—, —CH=CH—CH$_2$—O—, —(CH$_2$)$_2$CH=CH— or —CH=CH—(CH$_2$)$_2$—; $R^1$ is an alkyl group of 1 to 12 carbon atoms; $R^2$ is halogen, cyano, or trifluoroacetyl, or $R^2$ is alkyl, alkoxy, alkenyl, alkenyloxy, alkoxyalkyl, alkoxyalkoxy, alkenyloxyalkyl, alkenyloxyalkoxy, alkyloxyalkenyl or alkyloxyalkenyloxy each of such $R^2$ moieties being unsubstituted or fluorine substituted.

14. A electro-optical cell comprising:
(a) two plate means;
(b) liquid crystal means disposed between the two plate means and including a compound of the formula:

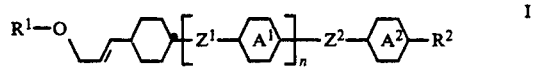

wherein rings $A^1$ and $A^2$ each independently are unsubstituted or halogen-substituted 1,4-phenylene, pyridin-2,5-diyl, pyrimidin-2,5-diyl, pyrazin- 2,5-diyl or trans-1,4-cyclohexylene or trans-1,3-dioxane; n is 0 or 1; $Z^1$ and $Z^2$ each independently are a single covalent bond or —CH$_2$CH$_2$—, —COO—, —OOC—, —OCH$_2$—, —CH$_2$O—, —(CH$_2$)$_4$—, —O(CH$_2$)$_3$—, —(CH$_2$)$_3$O—, the trans form of —O—CH$_2$—CH=CH—, —CH=CH—CH$_2$—O—, —(CH$_2$)$_2$CH=CH— or —CH=CH—(CH$_2$)$_2$—; $R^1$ is an alkyl group of 1 to 12 carbon atoms; $R^2$ is halogen, cyano, or trifluoroacetyl, or $R^2$ is alkyl, alkoxy, alkenyl, alkenyloxy, alkoxyalkyl, alkoxyalkoxy, alkenyloxyalkyl, alkenyloxyalkoxy, alkyloxyalkenyl or alkyloxyalkenyloxy, each of such $R^2$ moieties being unsubstituted or fluorine substituted; and (c) means for applying electric potential to said plate means.

15. A compound according to claim 1, having the formula

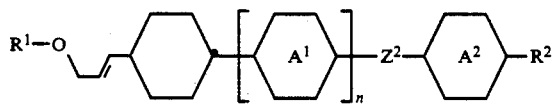

wherein ring $A^1$ is 1,4-phenylene or trans-1,4-cyclohexylene;

n is either 0 or 1; ring $A^2$ is 1,4-phenylene which is unsubstituted or halogen substituted; and $R^1$, $R^2$ and $Z^2$ are as defined in claim 1.

16. A compound according to claim 15, having the formula

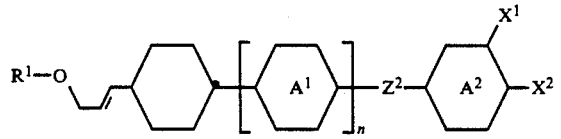

wherein $X^1$ is hydrogen, chlorine or fluorine, and $X^2$ is fluorine or chlorine.

17. A compound according to claim 1, having the formula

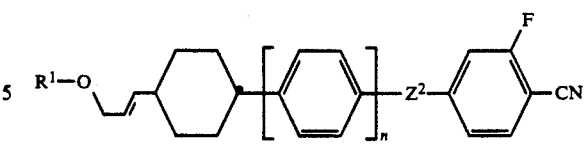

wherein $R^1$, n and $Z^2$ are as defined in claim 1.

18. A compound according to claim 1, having the formula

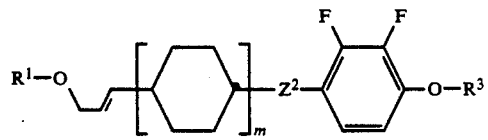

wherein m is either 1 or 2; $R^3$ is alkyl of 1 to 12 carbon atoms, alkenyl of 1 to 12 carbon atoms, or $R^3$ is fluoroalkyl; and $R^1$ and $Z^2$ are as defined in claim 1.

19. A compound according to claim 1, wherein $Z^1$ is either a single covalent bond, —CH$_2$CH$_2$—, or —COO—.

20. A compound according to claim 1, having the formula

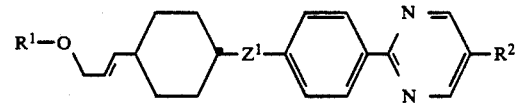

wherein $Z^1$ is either a single covalent bond or —COO—; and $R^1$ and $R^2$ are as defined in claim 1.

21. A compound according to claim 1, having the formula

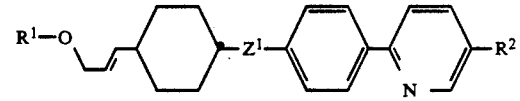

wherein $Z^1$ is either a single covalent bond or —COO—; and $R^1$ and $R^2$ are as defined in claim 1.

* * * * *